(12) United States Patent
Sjöberg

(10) Patent No.: US 10,932,814 B2
(45) Date of Patent: Mar. 2, 2021

(54) MULTI-LAYER DERMATOME

(71) Applicant: Folke Sjöberg, Linköping (SE)

(72) Inventor: Folke Sjöberg, Linköping (SE)

(73) Assignee: Seber AB, Stockholm (SE)

( * ) Notice: Subject to any disclaimer, the term of this patent is extended or adjusted under 35 U.S.C. 154(b) by 49 days.

(21) Appl. No.: 16/171,438

(22) Filed: Oct. 26, 2018

(65) Prior Publication Data

US 2019/0059924 A1    Feb. 28, 2019

Related U.S. Application Data

(63) Continuation of application No. PCT/SE2017/050423, filed on May 2, 2017.

(30) Foreign Application Priority Data

Apr. 29, 2016 (SE) .................................. 1650588-5

(51) Int. Cl.
*A61B 17/322* (2006.01)
*A61B 17/32* (2006.01)

(52) U.S. Cl.
CPC .... *A61B 17/322* (2013.01); *A61B 17/320068* (2013.01); *A61B 2017/320064* (2013.01)

(58) Field of Classification Search
CPC ............ A61B 17/32; A61B 17/320068; A61B 17/3211; A61B 17/3213; A61B 17/3215; A61B 17/322; A61B 2017/320064; A61B 2017/320071; A61B 2017/320089; A61B 2017/32113; A61B 2017/32116; B27B 19/006; B27B 19/008; B23D 61/006
USPC .................................................. 606/132, 166
See application file for complete search history.

(56) References Cited

U.S. PATENT DOCUMENTS

| 1,383,133 | A | * | 6/1921 | Lucke | ....................... | C14B 1/14 |
| | | | | | | 69/21.5 |
| 2,081,639 | A | * | 5/1937 | Perry | ........................ | B23C 1/00 |
| | | | | | | 409/132 |
| 5,846,244 | A | * | 12/1998 | Cripe | .................... | B27B 19/008 |
| | | | | | | 606/82 |
| 6,887,250 | B1 | | 5/2005 | Dority et al. | | |
| 2005/0222598 | A1 | * | 10/2005 | Ho | ......................... | A61B 17/32 |
| | | | | | | 606/171 |
| 2007/0244491 | A1 | | 10/2007 | Russell | | |
| 2011/0136075 | A1 | | 6/2011 | Park et al. | | |

FOREIGN PATENT DOCUMENTS

| EP | 2484298 A1 | 8/2012 |
| EP | 2604201 A1 | 6/2013 |

* cited by examiner

*Primary Examiner* — Kathleen S Holwerda
*Assistant Examiner* — Kankindi Rwego
(74) *Attorney, Agent, or Firm* — Gabriela B. Tomescu, Esq.; Bergenstråhle & Partners AB

(57) ABSTRACT

A dermatome (10) comprising at least two oscillating blades (20*a-d*) arranged parallel to each other and configured to simultaneously cut separate skin grafts (2*a-d*) at different depths from a donor site (1).

10 Claims, 6 Drawing Sheets

MULTI-LAYER DERMATOME

This application is the continuation of International Application No. PCT/SE2017/050423, filed 2 May 2017, which claims the benefit of Swedish Patent Application No. SE 1650588-5, filed 29 Apr. 2016, the entire contents of which are hereby incorporated by reference.

TECHNICAL FIELD

The present invention relates generally to a device for skin grafting, more particularly to a dermatome capable of simultaneously harvesting a plurality of skin grafts.

BACKGROUND ART

Autologous skin grafting, i.e., to harvest thin skin layers and transplant them into areas where the skin is missing due to skin damage caused by fire or other external force, is a standard operation above all in plastic surgery and burn care. This type of surgical procedure has been made since the early $20^{th}$ century, but has expanded dramatically after 1979, when the technology was successfully described for operational correction of skin defects due to above all burns (Janecovic, 1979). The technique used initially for limited injuries is now a standard technique for even very large skin defects regardless of the cause. Initially, the so-called drum dermatome was used, which had a drum like construction (cylinder) wherein the skin stuck on a tape-like drum and was thus lifted up toward the blade that cut thin slices which were collected. This technique was later abandoned for the "classic" dermatome, which has a vibrating or oscillating blade attached to a handle, which pushes the cutting knife in front of it like a reverse cheese slicer. The width of the blade is about 20 cm, and the oscillation of the blade can be powered either by an electric motor or compressed air. The skin is pre-treated with glycerol so that the knife design is able to slide on the skin surface while the operator presses it hard against the underlying skin. Given these manual operations, this is an art and requires training/skill to achieve good results. The dermatome currently dominant on the market is of such a design and made by Zimmer Inc., see e.g. EP 2 484 298 or US 2013/0018390.

However, there are several drawbacks and shortcomings with the known prior art. Normally, only the outermost thin layer of skin (the epidermis and part of the dermis) is harvested in a so-called split-thickness skin graft, up to a thickness of a few millimeters. The epidermis consists of the oldest cells, many of which are already dead and/or exhibiting cornification. Stem cells, which form the cornerstones for the formation of new skin, are almost completely missing in the epidermis. Furthermore, the harvested split-thickness skin graft only comprises parts of the dermis, which provides many of the basic mechanical properties of the skin, such as softness, elasticity and thickness. Also, other important components of skin transplantation are missing from the harvested split-thickness skin graft, such as hair follicles and sebaceous gland cells. When taking the split-thickness skin graft and moving it to the receiving area, a difficult abrasion arises at the donor site. This wound is sometimes what gives the patient more discomfort than the operated area before it is fully healed, above all in the form of pain, but also bleeding and the risk of infection. After healing, the donor site often takes on a cosmetic scarred appearance, which will remain lifelong and reminds the patient of the injury.

Another type of graft is a full-thickness skin graft which comprises both the epidermis and essentially all of the dermis and thereby including the above-mentioned components. However, the wound at the donor site will be considerably deeper and more difficult to heal. In addition, the thickness of the full-thickness skin graft makes it more difficult to preserve and handle before and during transplantation to the receiving area.

It has been found in preliminary studies that improved results in skin grafting can be achieved by taking multiple thin skin grafts from the same donor site, so-called laminated grafts, instead of the conventional split-thickness of full-thickness skin grafts. According to this technique, the top skin layer (epidermis) is not cut off, but replaced to the original location at the donor site to close the wound after harvesting and allowed to heal again. This leads to substantially reduced healing problems and scarring will be significantly less, i.e. improved results at the donor site.

The second, and possibly third and fourth, layer(s) that is harvested will contain substantially more dermis components, which both provide better mechanical properties at the receiving area, but also contributes more stem cells, which have a higher long-term healing potential as they can divide more times and give rise to new cells than the more superficially located skin cells in the epidermis. This or these layer(s) is/are then used on the injured area. Possibly, the harvested skin layers also contain hair follicles and sebaceous gland cells, which improve the cosmetic appearance of the healed skin long-term and additionally obviates the need for daily rubbing or moisturising the transplanted skin surfaces, as is the case with conventional skin transplants.

However, even if harvesting multiple skin grafts from one and the same donor site conceivably could be achieved using conventional dermatomes, a number of complications arise. Firstly, the operator needs to perform multiple passes with the dermatome at the donor site, with separate readjustments of the blade (graft thickness, angle etc.) for each pass, which is time-consuming. Furthermore, the blade being only adapted for single pass skin harvesting, the sharpness and precision of the blade of the dermatome deteriorates with multiple readjustments and passes over the skin. Also, this leads to increased risk of damage to the instrument. Additionally, conventional dermatomes are provided with width plates to adapt the width of the harvested skin, but the width of the blade is the same. Hence, during subsequent passes over the skin, there is a high risk of misalignment with the previous cut such that the blade glides over the edge of the non-cut skin to produce skewed and non-uniform cuts which ultimately lead to inferior skin grafts as well as poor healing and scarring at the donor site.

Hence, there is a need to develop improved devices for harvesting skin transplants which eliminates or alleviates the above problems.

SUMMARY OF INVENTION

An object of the present invention is to provide an improved device for harvesting skin which provides better healing characteristics both at the receiving injured area and at the donor site. This object is achieved by providing a dermatome comprising at least two oscillating blades arranged parallel to each other and configured to simultaneously cut separate skin grafts at different depths from a donor site. By arranging at least two blades parallel to each other and configured to simultaneously cut separate skin grafts at the donor site, multiple thin skin grafts may be harvested during one cutting operation, i.e. in one single pass with the dermatome over the skin. Hence the problems described above in connection with the single blade dermatome may be solved.

In a preferred embodiment, the blades are arranged spaced after each other in the cutting direction of the dermatome. The arrangement of consecutive blades provides a simple and easy-to-use construction for the dermatome to obtain the desired multiple skin grafts.

In an advantageous embodiment, the blades are arranged with increasing depth away from the cutting direction of the dermatome. The increasing depth of the blades enables simultaneous harvesting of skin grafts from different layers of skin.

In an alternative embodiment, the width of the blades decreases away from the cutting direction of the dermatome. By having consecutive smaller widths of the blades, the risk of a subsequent blade of the dermatome contacting or interfering with the edge on the non-cut skin is eliminated, thereby ensuring uniform skin grafts.

In a further preferred embodiment, the penetration depth of each blade is adjustable. Alternatively, the distance between each blade is adjustable. By providing the possibility to adjust the depth of and distances between each blade, a highly adaptive dermatome is achieved which may be used in various situations involving different patients and donor sites.

In an advantageous embodiment, the dermatome comprises a plurality of blades. The number of blades may be chosen depending e.g. on the thickness and composition of the skin surface at the donor site, with areas of the body with thicker skin allow for the use of more blades, thus producing more skin grafts.

In an alternative embodiment, the dermatome further comprises a collection surface for each blade arranged in an intermediate space between the blades, adapted to receive the harvested skin grafts. The collection surfaces facilitate protection and handling of each individual skin graft that is harvested.

BRIEF DESCRIPTION OF DRAWINGS

The invention is now described, by way of example, with reference to the accompanying drawings, in which.

DESCRIPTION OF EMBODIMENTS

In the following, a detailed description of an improved dermatome according to the present invention is provided.

Figure 1:
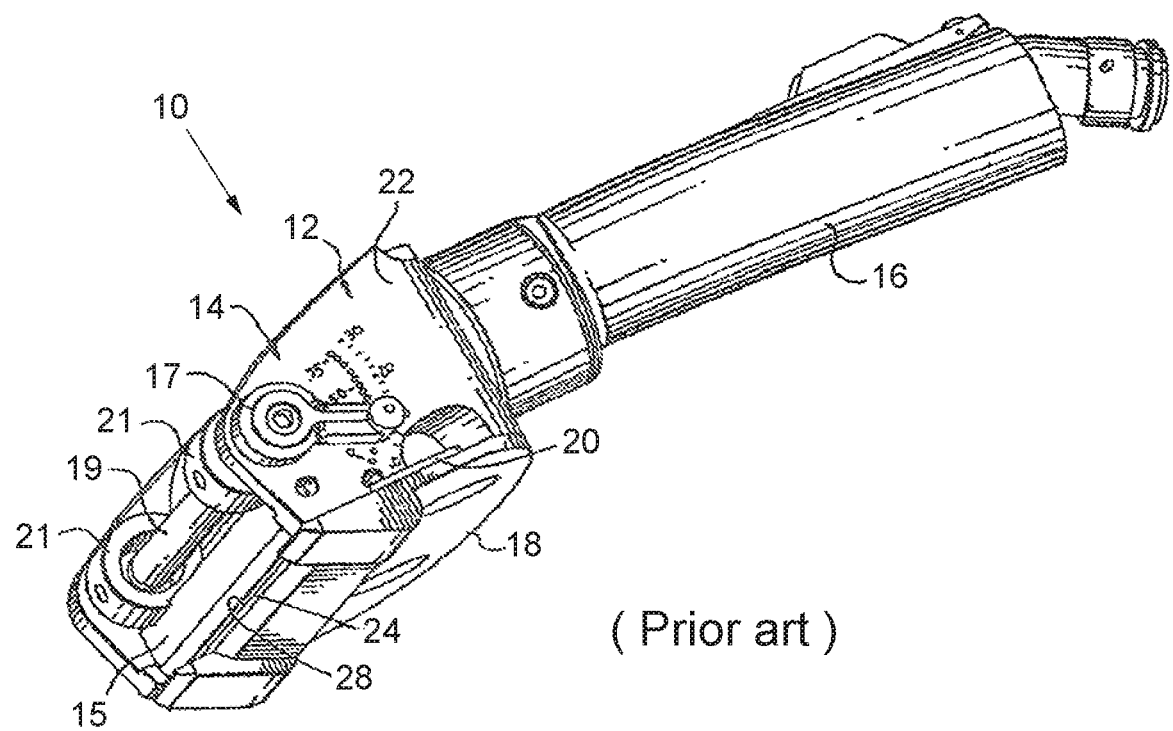
FIG. 1 shows a conventional dermatome known from the prior art.

FIG. 1 shows a conventional dermatome 10 known from the prior art described in EP 2 484 298 (the reference signs in this paragraph referring to that document). It comprises a main body 12 with a head 14 connected to a handle 16. The dermatome further comprises a blade assembly 20 including a flat blade 24 with a sharp front edge 28 facing forward across the dermatome. In operation, the blade is oscillated in a transverse direction by means of an electrical drive or compressed air to form a side-to-side slicing action as the dermatome is pressed against the skin at the donor site and pushed forward. The blade is arranged perpendicular to the cutting direction and may extend the entire or part of the width of the cutting head assembly. Arranged slightly forward and above the blade is a member 19 with a pair of rotating cams 21 engaging a control bar 15 which controls the distance between the control bar and the blade edge. During skin grafting, the cut skin tissue moves rearward between the control bar and the blade and up along a slanted collection surface to protect and facilitate handling of the skin graft.

As a further inspiration for the present invention, the inventor has looked to the field of carpentry, more particularly to hand planes used for shaping wood surfaces. The dermatome according to the present invention has been conceived with such hand plane tools in mind, but with the addition of more blades.

The concept that the inventive idea is based on is to construct a new skin grafting device for skin transplants which through its construction eliminates the above shortcomings associated with the prior art. This is achieved with a dermatome comprising a plurality of cutting surfaces disposed parallel consecutively after one another in a device more or less similar to the conventional, previously described dermatome comprising a handle-like holder with a head, simultaneously cutting a number of slices of the skin, the number of slices is chosen according to the thickness of the skin at the donor site, i.e. dorsal thicker skin allows for more slices, while the thickness of the skin on the inside of the forearm or inner thigh is limited and can only offer a maximum of 2 slices. In one example, as many as 5 blades is provided.

In accordance with the dermatome according to the present invention, it is foreseen that the uppermost, top layer of skin is not severed during harvesting the skin graft(s), but instead is replaced to its original location and allowed to heal, thereby closing the wound. This significantly reduces the problems of healing and scarring at the donor site.

Simultaneously with cutting the top layer, one or more additional slices of skin, containing substantially more components of the dermis, are also cut by the plurality of additional blades of the dermatome. The blades are arranged parallel and consecutively, but spaced, after one another in the cutting assembly of the dermatome. The intermediate space between the blades provides a slanted collection surface for the harvested skin grafts, such that the cut slices of skin may slide along the collection surface without being damaged. Thereby each individual skin slice is collected separately to facilitate subsequent handling and preservation until a skin transplant is performed.

The blades of the dermatome may be individually adjusted to vary the penetration depth and spacing to adjacent blades. Thereby, it is possible to achieve a thin top layer of e.g. 6 thousands of an inch (0.1524 mm) that is to be replaced after harvesting. The depth and spacing of each blade is set with high precision to achieve the necessary quality of the harvested skin grafts.

Advantageously, the blades may be arranged to protrude at different depths to enable harvesting skin grafts at different depths of the skin. As shown schematically in FIG. 2, the blades are arranged at increasing depth in a direction away from the cutting direction of the dermatome, i.e. from the front to the rear of the cutting assembly contacting the skin. Also illustrated in FIG. 2, the width of the blades decreases away from the cutting direction of the dermatome such that the rearmost blade having the biggest penetration depth has the smallest width.

In operation, the operator presses the dermatome with the at least two blades against the skin at the donor site. The first, front blade will then cut the top layer of skin which slides up on the slanted collection surface. At the same time, the second, rear blade follows in the exact same cutting path defined by the front blade, to harvest an underlying layer of skin. This harvested skin graft will then slide up on the collection surface associated with the second blade to be removed. After the harvesting procedure is ended, the top layer is retrieved from the front collection surface and replaced to the donor site. The procedure is then the same for each additional cutting blade of the dermatome assembly.

Figure 3:
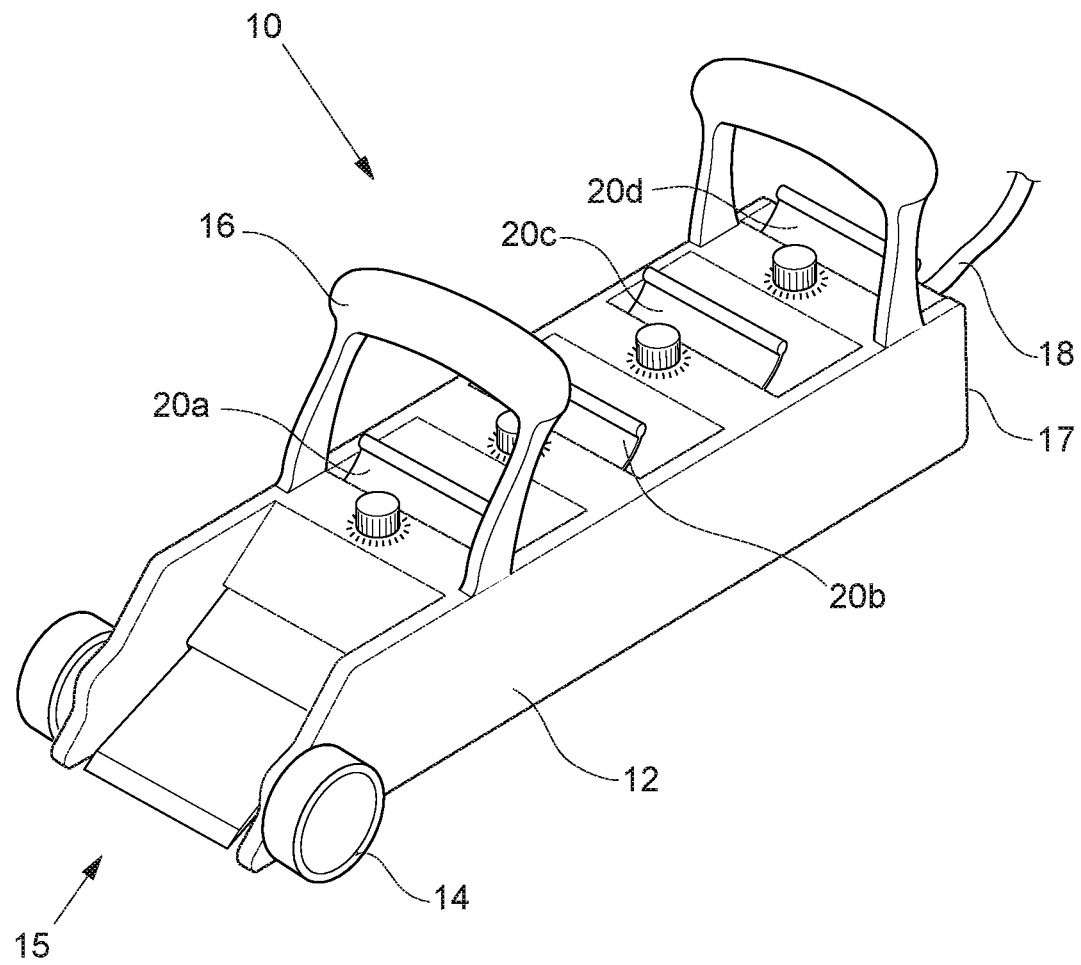
FIG. 3 shows a perspective view of an exemplary embodiment of a dermatome according to the present invention.

FIG. 3 illustrates one exemplary embodiment of a dermatome 10 according to the present invention in a perspective view. This representation should not be interpreted as limiting in any way, but merely used to illustrate one possible realisation of the dermatome. The dimensions of the apparatus and components have been exaggerated to better illustrate the functionality. However, it should be understood that the dermatome 10 may be made more compact to fit the desired application or setting in which it is to be used.

The dermatome 10 comprises four blades 20a-d mounted one after the other and substantially parallel to each other on a main body 12. The main body 12 is provided with a pair of handles 16. At the rear end 17 of the main body 12, a connection line 18 for supply of electrical power and/or compressed air to the main body 12 is provided. At the front end 15 of the main body 12 there is provided a pair of rollers 14 which are arranged to be pressed against the skin surface 1 during operation of the dermatome 10, in order to achieve a smooth surface for harvesting skin transplants.

Figure 4A:
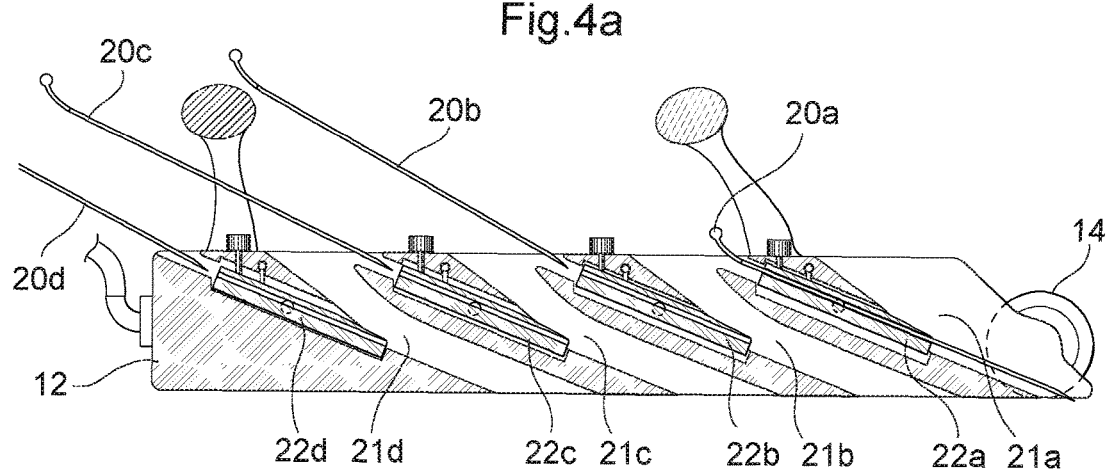
FIGS. 4a-b shows a cross-sectional view of the dermatome in FIG. 3.
Figure 4B:
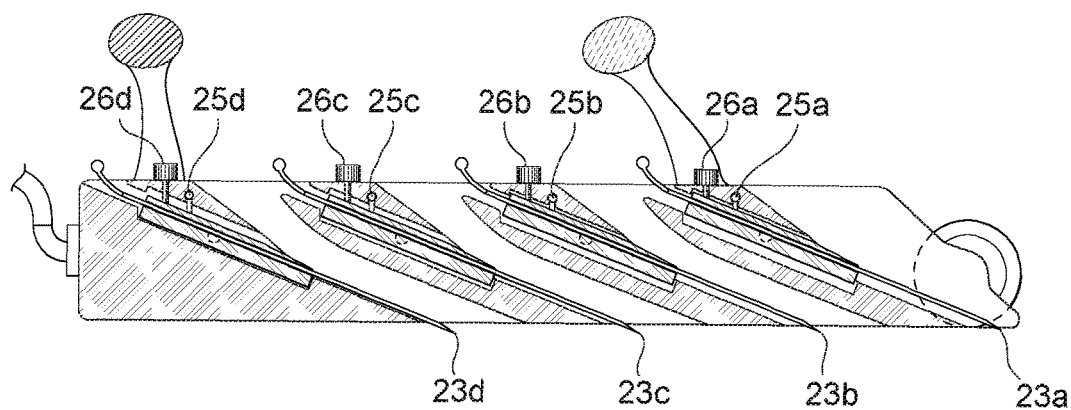

Turning now to FIGS. 4a-b, each of the blades 20a-d are mounted in a respective slot 21a-d of the main body 12. The slots 21a-21d provide respective through-going passages in the main body 12 giving access to the skin surface underneath the dermatome 10 in operation. As may be seen in FIG. 4a, the blades 20a-d are mounted in respective brackets or attachments 22a-d such that a front sharp edge 23a-d faces in the forward direction of the dermatome 10. The brackets 22a-d are arranged to hold and maintain the respective blades 20a-d in a desired position with the aid of locking means 24a-d. The locking means 24a-d may be in the form of a snap-fit connection or a resilient member adapted to engage in a corresponding hole or recess in the blade 20a-d. Furthermore, the brackets 22a-d are connected to the main body by means of reciprocating drive pins 25a-d which may be driven by respective motors (not shown) in the main body 12 as known in the art. Each motor is arranged to drive the respective drive pin 25a-d which then transfers an oscillating motion to the respective brackets 22a-d and blades 20a-d to provide the cutting action.

In FIG. 4a, the front or first blade 20a is shown mounted in its bracket 22a and ready to cut the first top layer of skin. The subsequently following blades 20b-d are here shown in a position before being mounted in the corresponding brackets 22b-d.

FIG. 4b shows all the blades 20a-d mounted in their corresponding brackets 22a-d. In order to cut successive skin transplants or slices at different depths during one passage of the dermatome 10, the respective blades 20a-d are adapted to be mounted at and/or adjustable to different heights with respect to the main body 12. This is achieved by means of a height adjustment member 26a-d in the form of a rotatable knob which interacts with the corresponding brackets 22a-d. As may be seen in FIG. 4b each of the blades 20b-d is mounted to protrude deeper than the corresponding preceding blade 20a-c, respectively, to be able to reach its target skin layer at a predetermined depth.

Figure 2:
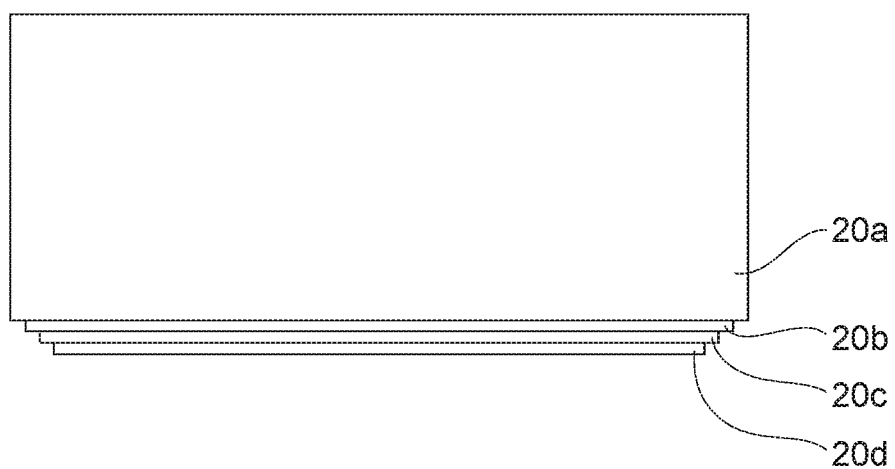
FIG. 2 shows a schematic representation of an arrangement of a plurality of blades in a dermatome according to the present invention
Figure 5:
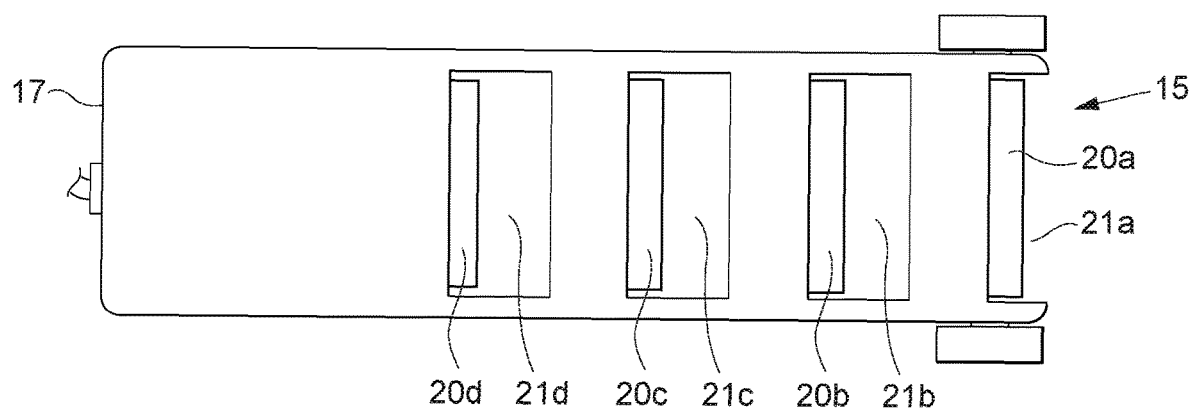
FIG. 5 shows a bottom view of the dermatome in FIG. 3.

As previously described in relation to FIG. 2, the blades 20a-d have different widths, such that the first blade 20a arranged nearest to the front end 15 is wider than the second blade 20b. As may be seen in FIG. 5, the width of the blades 20a-d decreases in a rearward direction on the dermatome 10 from the front end 15 to the rear end 17 of the main body 12, i.e. opposite the cutting direction. The decreasing width of the blades 20a-d facilitates cutting uniform skin grafts, since each trailing blade 20b-d will be able to follow in the path of the preceding blade 20a-c without the risk of snagging or engaging the edges of the path cut by the preceding blade 20a-c.

Figure 6A:
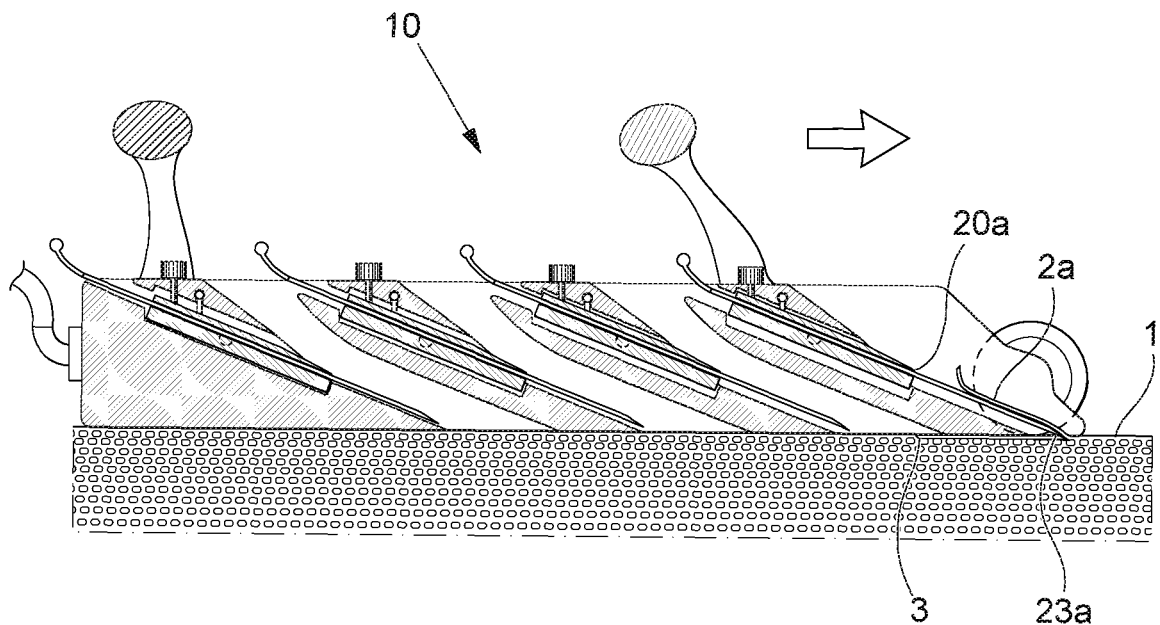
FIGS. 6a-f shows a cross-sectional view of the dermatome in FIG. 3 at different stages of operation.

An exemplary method of operating the dermatome 10 according to the present invention will now be explained with reference to FIGS. 6a-f. FIG. 6a shows a first stage or phase of operation wherein the dermatome 10 has been pressed against the skin surface 1 at the donor site of the patient. The dermatome 10 is then moved forward in the direction of the arrow. Here, only the first blade 20a is engaging the skin surface to cut a first top layer 2a of the skin corresponding to the epidermis as explained above. The remaining blades 20b-d are mounted into their corresponding brackets 22b-d, but have not been fully inserted to a cutting position.

Figure 6B:
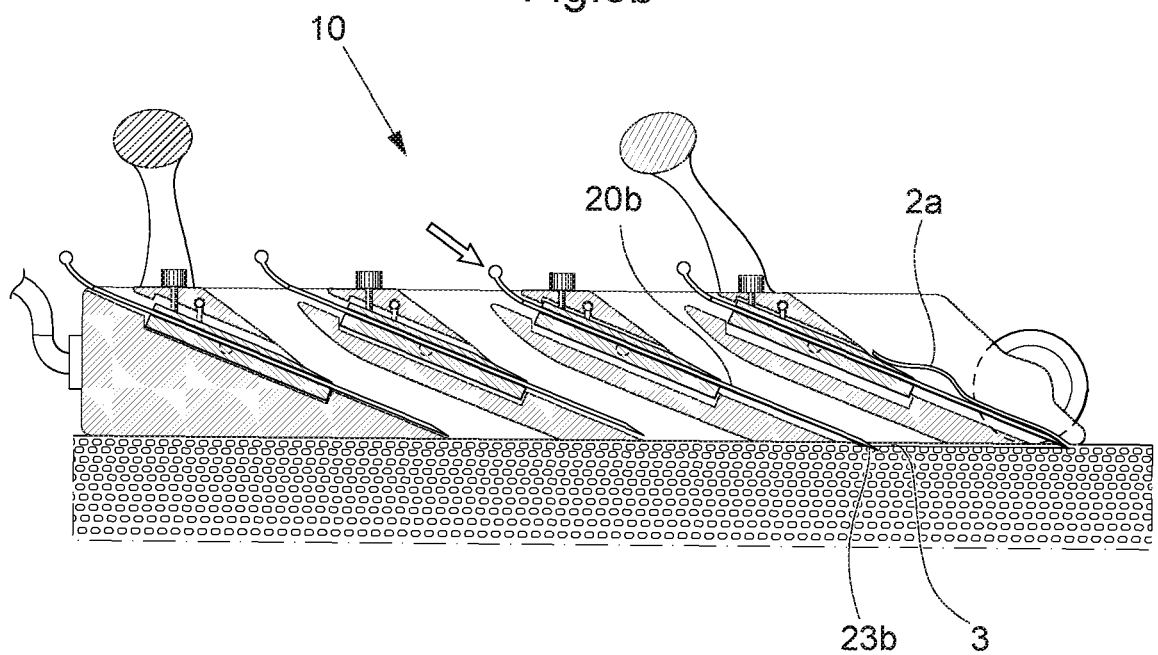

Subsequently, in FIG. 6b, the dermatome 10 has been moved a distance forward along the skin surface 1 and a corresponding length of the top skin layer 2a has been cut by the first blade 20a. In this position, the sharp edge 23b of the second blade 20b is aligned with the trailing edge 3 (i.e. starting point) of the path cut by the first blade 20a. at this stage, the operator may insert the second blade 20b to a cutting position, as indicated by the arrow, deeper than the first blade 20a, such that the sharp edge 23b is in position to cut a second layer 2b of skin corresponding to the dermis as explained above. This procedure is then repeated with each of the subsequent blades 20c and 20d when the respective sharp edges 23c and 23d are aligned with the trailing edge 3 of the path cut by the preceding blades 20a and 20b as the dermatome 10 is moved forward.

Figure 6C:
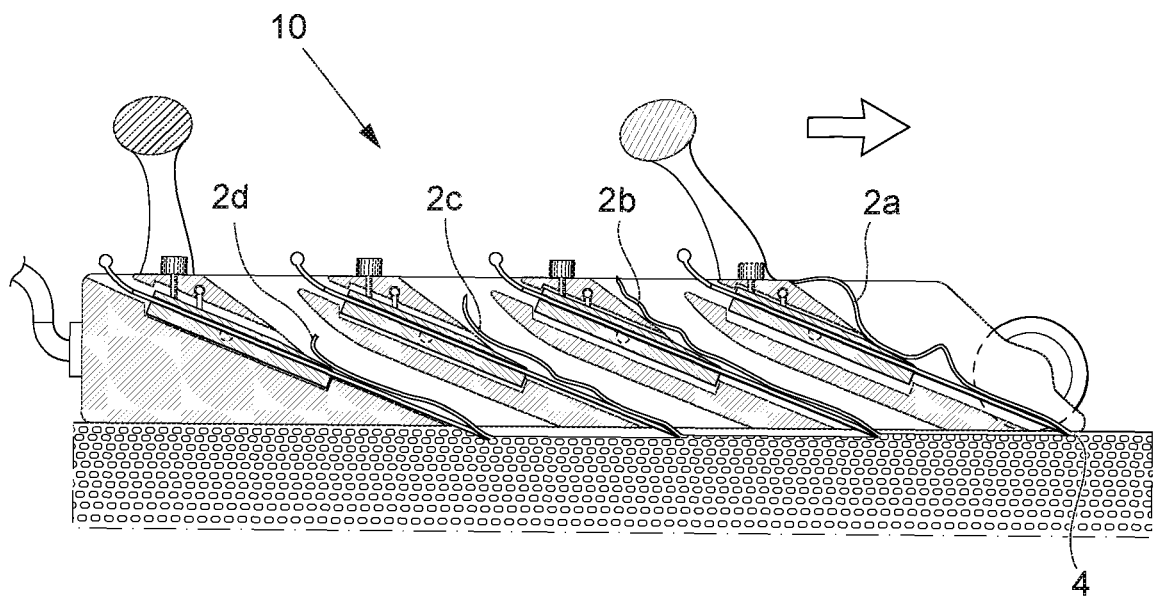

In FIG. 6c, the dermatome 10 has been moved further forward and all of the blades 20a-d are fully inserted in the cutting position to cut respective layers of skin 2a-d. The harvested layers of skin 2a-d are here shown as sliding up through the respective slots 21a-d on the main body to be harvested (layers 2b-d) or replaced (layer 2a).

Figure 6D:
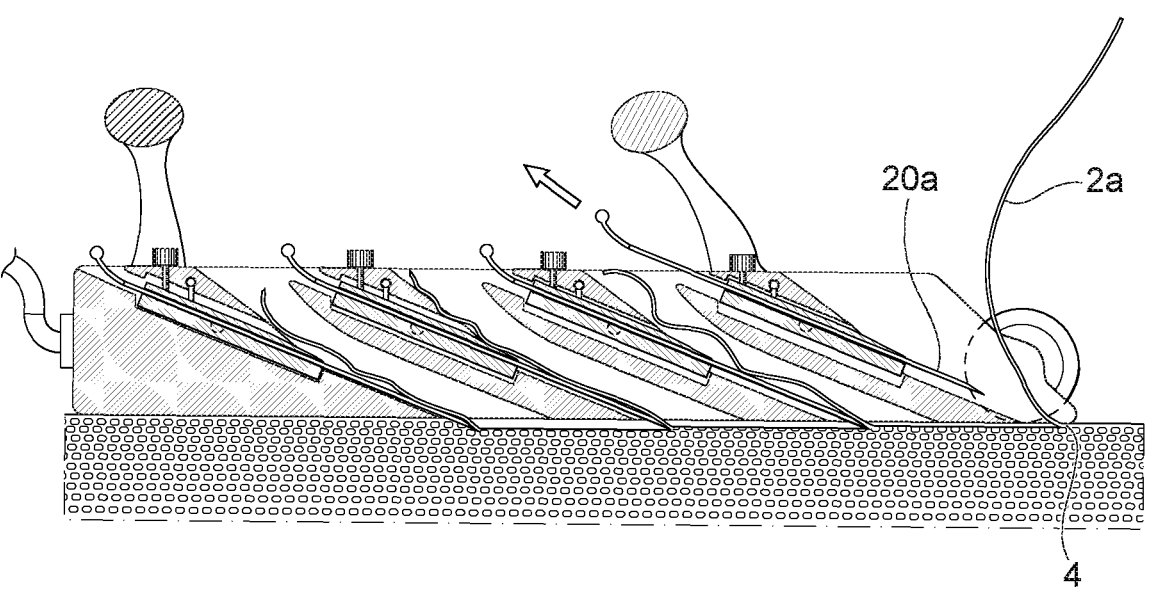

In FIG. 6d, the sharp edge 23a of the first blade 20a has reached the end point 4 (leading edge) of the path corresponding to the desired length of the skin grafts to be harvested. At this position, the first blade 20a is retracted from the cutting position as indicated by the arrow. The top skin layer 2a may now be folded in the forward direction so as not to interfere with continued skin grafting operation. The remaining blades 20b-d are maintained in the cutting position and the dermatome 10 is moved further forward. This procedure is then repeated for each subsequent blade 20b-d as the corresponding sharp edges 23b-d become aligned with the leading edge 4 of the path. The subsequent layers of skin 2b-d to be harvested may be severed and removed from the dermatome 10 through the respective slots 21b-d in the main body 12 to avoid clinging to the first top skin layer 2a.

Figure 6E:
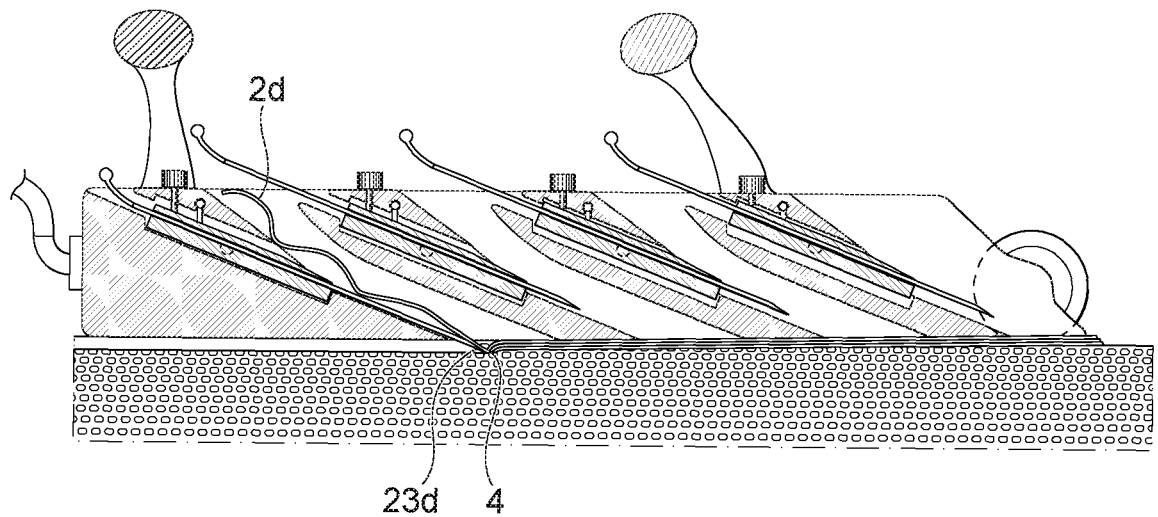
Figure 6F:
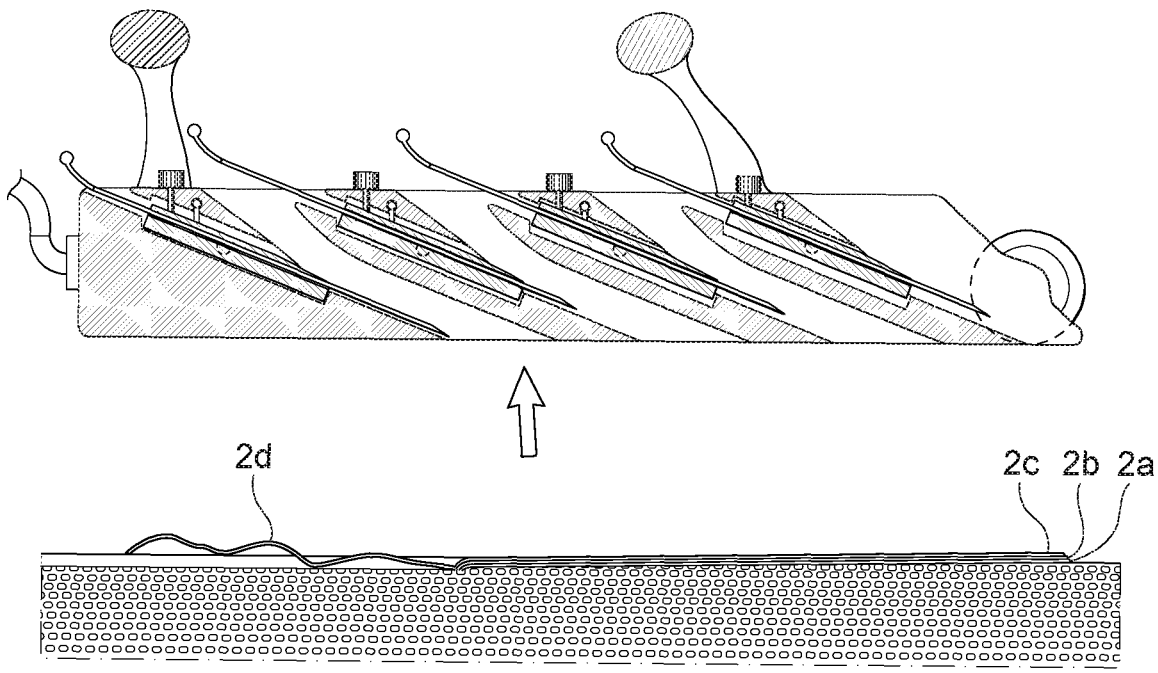

In FIG. 6e, the sharp edge 23d of the fourth and last blade 20d has reached the leading edge 4. At this point, the skin grafting operation is terminated and the dermatome 10 is removed from the skin surface, as indicated by the arrow in FIG. 6f.

The invention claimed is:

1. A dermatome comprising a main body connected to a handle and at least two blades arranged parallel to each other and configured to be oscillated in a transverse direction in relation to the main body to simultaneously cut separate skin grafts at different depths from a donor site on the body of a patient when the dermatome is pressed against the skin at the donor site.

2. The dermatome according to claim 1, wherein the at least two blades are arranged spaced after each other in the cutting direction of the dermatome.

3. The dermatome according to claim 1, wherein the at least two blades are arranged with increasing depth away from the cutting direction of the dermatome.

4. The dermatome according to claim 1, wherein the width of the at least two blades decreases away from the cutting direction of the dermatome.

5. The dermatome according to claim 1, wherein the penetration depth of each of the at least two blades is adjustable.

6. The dermatome according to claim 1, wherein the distance between each of the at least two blades is adjustable.

7. The dermatome according to claim 1, wherein the at least two blades are arranged to oscillate out of phase with each other.

8. The dermatome according to claim 1, wherein the at least two blades are arranged to oscillate at different frequencies.

9. The dermatome according to claim 1, wherein at least one of the at least two blades comprises a serrated cutting edge.

10. The dermatome according to claim 1, further comprising a collection surface for each of the at least two blades arranged in an intermediate space between the at least two blades, adapted to receive the harvested skin grafts.

* * * * *